(12) United States Patent
Knudson et al.

(10) Patent No.: US 7,201,757 B2
(45) Date of Patent: Apr. 10, 2007

(54) GASTRO-ESOPHAGEAL REFLUX DISEASE (GERD) TREATMENT METHOD AND APPARATUS

(75) Inventors: Mark B. Knudson, Shoreview, MN (US); Katherine S. Tweden, Mahtomedi, MN (US); Timothy R. Conrad, Eden Prairie, MN (US); John P. Sopp, Forest Lake, MN (US)

(73) Assignee: EnteroMedics Inc., St. Paul, MN (US)

( * ) Notice: Subject to any disclaimer, the term of this patent is extended or adjusted under 35 U.S.C. 154(b) by 0 days.

(21) Appl. No.: 10/600,088

(22) Filed: Jun. 20, 2003

(65) Prior Publication Data

US 2004/0260316 A1 Dec. 23, 2004

(51) Int. Cl.
*A61B 17/08* (2006.01)
(52) U.S. Cl. .................. 606/151; 606/157; 128/898
(58) Field of Classification Search ............ 606/139, 606/140, 151, 157; 128/898
See application file for complete search history.

(56) References Cited

U.S. PATENT DOCUMENTS

| | | | |
|---|---|---|---|
| 4,218,814 A * | 8/1980 | Hodapp | ............ 29/450 |
| 4,403,604 A | 9/1983 | Wilkinson et al. | |
| 4,592,339 A * | 6/1986 | Kuzmak et al. | ............ 128/899 |
| 4,846,836 A | 7/1989 | Reich | |
| 5,006,106 A | 4/1991 | Angelchik | |
| 5,074,868 A | 12/1991 | Kuzmak | |
| 5,226,429 A | 7/1993 | Kuzmak | |
| 5,403,326 A | 4/1995 | Harrison et al. | |
| 5,549,621 A | 8/1996 | Bessler et al. | |
| 5,771,903 A | 6/1998 | Jakobsson | |
| 5,861,014 A | 1/1999 | Familoni | |
| 5,919,233 A | 7/1999 | Knopf et al. | |
| 6,074,341 A | 6/2000 | Anderson et al. | |
| 6,098,629 A | 8/2000 | Johnson et al. | |
| 6,104,955 A | 8/2000 | Bourgeois | |
| 6,432,040 B1 | 8/2002 | Meah | |
| 6,450,173 B1 | 9/2002 | Forsell | |
| 2002/0193842 A1 * | 12/2002 | Forsell | ............ 607/40 |
| 2003/0144709 A1 | 7/2003 | Zabara et al. | |
| 2003/0208212 A1 * | 11/2003 | Cigaina | ............ 606/151 |

(Continued)

FOREIGN PATENT DOCUMENTS

WO      WO 01/41671 A2 *  6/2001

OTHER PUBLICATIONS

Crookes, P. et al., "The Angelchik Prosthesis: What Have We Learned in Fifteen Years?," *Ann Thorac Surg*, vol. 57, pp. 1385-1386 (1994).

(Continued)

*Primary Examiner*—Michael J. Hayes
*Assistant Examiner*—Michael G Mendoza
(74) *Attorney, Agent, or Firm*—Merchant & Gould P.C.

(57) ABSTRACT

The method of the invention includes accessing a juncture of an esophagus and a stomach of the patient on a distal side of a diaphragm. The esophagus and a fundus of the stomach intersect at a cardiac notch located at an original cardiac notch position. A reducing element is placed at the junction with the reducing element selected to reposition the cardiac notch to a position more distal to a lower esophageal sphincter of the patient.

12 Claims, 3 Drawing Sheets

U.S. PATENT DOCUMENTS

2004/0039425 A1     2/2004     Greenwood-Van Meerveld

OTHER PUBLICATIONS

Curley, S. et al., "Late Complications After Gastric Reservoir Reduction With External Wrap," *Arch Surg*, vol. 122, pp. 781-783 (Jul. 1987).

DeVault, K. et al., "Practice Guidelines: Updated Guidelines for the Diagnosis and Treatment of Gastroesophageal Reflux Disease," *AJG*, vol. 94, No. 6, pp. 1434-1442 (1999).

Evans, D. et al., "An objective long-term evaluation of the Angelchik antireflux prosthesis," *Annals of the Royal College of Surgeons of England*, vol. 73, pp. 355-360 (1991).

Gray, H. et al., "The Digestive System," *Anatomy of the Human Body*, Thirtieth American Edition, pp. 1446, date unknown.

Hinder, R. et al., "Laparoscopic Nissen Fundoplication Is an Effective Treatment for Gastroesophageal Reflux Disease," *Annals Of Surgery*, vol. 220, No. 4, pp. 472-483 (Oct. 1994).

Hunt, R., "The relationship between the control of pH and healing and symptom relief in gastro-oesophageal reflux disease," *Aliment Pharmacol Ther*, vol. 9, Suppl. 1, pp. 3-7 (1995).

Kozarek, R. et al., "An Anti-Reflux Prosthesis in the Treatment of Gastroesophageal Reflux," *Annals of Internal Medicine*, vol. 98, pp. 310-315 (1983).

Lafullarde, T. et al., "Laparoscopic Nissen Fundoplication: Five-Year Results and Beyond," *Arch Surg*, vol. 136, pp. 180-184 (Feb. 2001).

Mattar, S. et al., "M1910: Short-Term Outcome of Collis-Nissen Gastroplasty Using A Wedge Gastroplasty Technique," *DDW AstraZeneca*, 1 pg. (May 2003).

Perdikis, G. et al., "Laparoscopic Nissen Fundoplication: Where Do We Stand?," *Surgical Laparoscopy & Endoscopy*, vol. 7, No. 1, pp. 17-21 (1997).

Rantanen, T. et al., "The Long Term Results of Open Antireflux Surgery in a Community-Based Health Care Center," *The American Journal of Gastroenterology*, vol. 94, No. 7, pp. 1777-1781 (1999).

Rothstein, R. et al., "Endoscopic suturing for gastroesophageal reflux disease: clinical outcome with the Bard EndoCinch," *Gastrointest Endoscopy Clin N Am*, vol. 13, pp. 89-101 (2003).

Schauer, P. et al., "Surgical Management of Gastroesophageal Reflux Disease in Obese Patients," *Seminars in Laparoscopic Surgery*, vol. 8, No. 4, pp. 256-264 (Dec. 2001).

Wilkinson, L. et al., "Gastric (Reservoir) Reduction for Morbid Obesity," *Arch Surg*, vol. 116, pp. 602-605 (May 1981).

Kilgore, K. et al., "Nerve Conduction Block Utilising High-Frequency Alternating Current," *Medical & Biological Engineering & Computing*, vol. 42, pp. 394-406 (2004).

Product Brochure, "ATROSTIM Phrenic Nerve Stimulator," AtroTech Oy, P.O. Box 28, FIN-33721 Tampere, Finland, 2 pages (Jun. 2004).

Carugno, F. et al., "Development of an Adjustable Prosthesis for the Treatment of Gastroesophageal Reflux—Preliminary Results in a Porcine Model," *ASAIO Journal*, pp. 140-143 (1998).

Steinbrook, "Surgery for Severe Obesity", *New England Journal of Medicine*, vol. 350, pp. 1075-1079 (2004).

\* cited by examiner

GASTRO-ESOPHAGEAL REFLUX DISEASE (GERD) TREATMENT METHOD AND APPARATUS

I.

BACKGROUND OF THE INVENTION

1. Field of the Invention

This invention pertains to the field of treatment of gastro-esophageal reflux disease (GERD). More specifically, this invention pertains to a method and apparatus for treating of GERD by lengthening an esophagus.

2. Description of the Prior Art

A. GERD

Gastro-esophageal reflux is a physical condition in which stomach acids reflux, or flow back from the stomach into the esophagus. Frequent reflux episodes may result in a more severe problem known as gastro-esophageal reflux disease (GERD). GERD is the most common form of dyspepsia, being present in approximately 40% of adults in the United States on an intermittent basis and some 10% on a daily basis as described in U.S. Pat. No. 6,098,629 Johnson et al., dated Aug. 8, 2000.

As indicated in Johnson et al., heartburn is defined as a burning sensation or discomfort behind the breastbone or sternum and is the most common symptom of GERD. Other symptoms of GERD include dysphasia, odynophagia, hemorrhage, water brash and pulmonary manifestations such as asthma, coughing, or intermittent wheezing due to acid aspiration.

GERD is generally considered to be the result of a motility disorder which permits the abnormal and prolonged exposure of the esophageal lumen to acidic gastric contents. Hunt, "The Relationship between the Control of pH and Healing and Symptom Relief in Gastro-Oesophageal Reflux Disease", *Ailment Pharmacol Ther.*, 9 (Suppl. 1) pp. 3–7 (1995). Many factors are believed to contribute to the onset of GERD. These include transient lower esophageal sphincter (LES) relaxations, decreased LES resting tone, delayed stomach emptying and an ineffective esophageal clearance.

B. GERD Treatments

A summary of a number of GERD treatments can be found in DeVault, et al., "Updated Guidelines for the Diagnosis and Treatment of Gastroesophageal Reflux Disease", *Amer. J. of Gastroenterology*, Vol. 94, No. 6, pp. 1434–1442 (1999). The elusive nature and complexity of GERD is evidenced by the numerous attempts and suggestions for treatment and the continuing need for treatment techniques.

a. Lifestyle Changes

Treatments for GERD include lifestyle changes such as weight loss, avoidance of certain foods (e.g., coffee, caffeine, alcohol, chocolate) that exacerbate the symptoms of GERD and avoidance of excessive bending. Elevation of the head of a patient's bed helps prevent nocturnal reflex. While these avoidance strategies may be helpful, there is relatively little data pointing to the efficacy of lifestyle modification for the treatment of GERD.

b. Medicine

Certain medications used for treatment of GERD have been administered for years with varying success. Conventional antacids such as Tums® and Rolaids® may, in some patients, produce short-term relief but often have side effects including diarrhea and constipation.

Other drugs have been more effective at controlling GERD, but fail to treat underlying causes of the disease and have been proven to be extremely expensive and not readily available to all patients due to such expense. Examples of such drugs are $H_2$-receptor antagonists (which control gastric acid secretion in the basal state) and proton pump inhibitors (which control meal-stimulated acid secretion). Hunt, supra. Both classes of drugs can raise intragastric pH to about 4 for varying durations. Hunt, supra.

c. Surgery

A. Fundoplication

A traditional surgical treatments for GERD is fundoplication. Normally performed as an open surgical approach, fundoplication includes wrapping an upper portion of the stomach (the fundus) around a lower portion of the esophagus in the region of the LES.

The region of the esophagus near the LES junction is commonly referred to as the Z-line. At this location, the tissue of the esophagus merges with the tissue of the stomach. Commonly, this location is below the diaphragm of the patient. However, in some patients, this location may reside above the esophageal hiatus (the opening in the diaphragm through which the esophagus passes) requiring surgery in the thoracic cavity of the patient. Also, this location is in close proximity to vital structures such as nerves and blood vessels.

Fundoplication can treat GERD effectively in many patients for a period of time. In most cases, the patient returns to drug treatment after a length of time following surgery. Further, the surgery includes risks and common side affects of heartburn, dysphagia and gas bloat. Laparoscopic procedures for treatment of GERD include those disclosed in U.S. Pat. No. 5,403,326 to Harrison et al. dated Apr. 4, 1995. Laparoscopic procedures are complicated by close proximity to vessels and nerves as described above. Endoscopic procedures are also known which cinch and suture tissue of the esophagus An example of an endoscopic product is the EndoCinch™ system of C.R. Bard company.

Surgical procedures suffer from a high complication rate. Commonly. Surgical patients revert to a continuing need for drug therapy. Lafullarde, et al., "Laparoscopic Nissen Fundoplication: Five-Year Results And Beyond", *Arch. Surg.*, pp. 180–184 (2001); Hinder, et al., "Laparoscopic Nissen Fundoplication Is an Effective Treatment for Gastroesophageal Reflux Disease", *Ann. Surg.*, pp. 472–483 (1994); Perdikis, et al., "Laparoscopic Nissen Fundoplication: Where Do We Stand?", *Surg. Laparosc. Endosc.*, pp. 17–21 (1997); and Rantanen, et al., "The Long Term Results of Open Antireflux Surgery in a Community-Based Health Care Center", *Am. J. Gastroenterol.*, pp. 1777–1781 (1999).

B. LES Bulking

Less invasive surgical treatments for GERD and include techniques for bulking the lower esophageal sphincter. Such a technique is described in U.S. Pat. No. 6,098,629 Johnson et al, Aug. 8, 2000. Johnson et al. discloses bulking through an injected polymer in the esophagus. A polymer injection is the basis of the Enteryx™ and Gatekeeper™ systems of the Boston Scientific and Medtronic companies, respectively. Supporting the LES through radiofrequency induced scarring is the basis of the Strettar™ system of the Curon company.

C. LES Banding

Surgical techniques for the treatment of GERD have also included placement of restriction devices around the esophagus in attempts to compensate for an incompetent lower esophageal sphincter (LES). An example of such is shown in U.S. Pat. No. 5,919,233 to Knoph et al dated Jul. 6, 1999, and U.S. Pat. No. 5,006,106 to Angelchik dated Apr. 9, 1991.

The devices of the '233 and '106 patents are restrictions placed around the esophagus at the location of the incompetent LES. Such devices may slip during use. Further, such devices have a problem of requiring dissection around the LES junction. Crookes, et al., "The Angelchik Prosthesis: What Have We Learned in Fifteen Years?", *Ann. Thorac. Surg.,* pp. 1385–1386 (1994); Evans et al., "An Objective Long-Term Evaluation of the Angelchik Antireflux Prosthesis", *Annals of the Royal Colege of Surgeons of England,* pp. 355–360 (1991); and Kozarek et al., "An Anti-Reflux Prosthesis in the Treatment of Gastroesophageal Reflux", *Annals of Internal Medicine,* pp. 310–315 (1983).

Other suggested treatments include placement of an adjustable band around the esophagus. These are shown in U.S. Pat. No. 6,450,173 to Forsell and U.S. Pat. No. 6,432,040 to Meah dated Aug. 13, 2002.

D. Pacing

Other suggested treatment techniques include placement of pacemakers for stimulating muscle contractions in the esophageal sphincter, the stomach muscles or in the pyloric valve. U.S. Pat. No. 6,104,955 to Bourgeois dated Aug. 15, 2000 and U.S. Pat. No. 5,861,014 to Familoni dated Jan. 19, 1999.

E. Esophageal Lengthening

Surgical treatment has also included the Collis-Nissen gastroplasty for patients with short esophagus. Mattar, et al., "Short-Term Outcome of Collis-Nissen Gastroplasty Using a Wedge Gastroplasty Technique", Abstract No. M1910, Digestive Disease Week (DDW) (Joint meeting of Amer. Assoc. for the Study of Liver Diseases, Amer. Gastroenterological Assoc., Amer. Soc. For Gastrointestinal Endoscopy, Soc. For Surg. Of the Alimentary Tract) (May 17–22, 2003). In the Collis-Nissen gastroplasty, a portion of the stomach is removed to lengthen a foreshortened esophagus by approximately 3–4 centimeters. This creates an extended esophageal portion (referred to as a neo-esophagus) and has resulted in a reduction of GERD in some patients.

F. Obesity Treatments

From time-to-time, obesity treatments have demonstrated an impact on GERD. Such treatments include placement of bands (referred to as LAP bands) around the stomach. An example of a LAP band is shown in U.S. Pat. No. 5,266,429 to Kuzmak dated Jul. 13, 1993. LAP bands and other gastric bandings are disclosed in Schauer, et al, "Surgical Management of Gastroesophageal Reflux Disease in Obese Patients", Seminars in Laparoscopic Surgery, Volume 8, Number 4, pages 256–264 (2001). Such LAP bands wrap around a portion of the fundus to create a greatly reduced volume portion of a fundus above the LAP band. Such bands create an upper chamber above the band to create a sensation of satiation after consuming only a small volume of food. See also, U.S. Pat. No. 5,549,621 to Bessler et al., dated Aug. 27, 1996; U.S. Pat. No. 5,226,429 to Kuzmak dated Jul. 13, 1993; and U.S. Pat. No. 4,592,339 to Kuzmak et al. dated Jun. 3, 1986.

Notwithstanding multiple attempts at various types of treatment, GERD continues to be a serious disease proving to be difficult to treat by any of the foregoing prior art techniques. In view of the foregoing and notwithstanding various efforts exemplified in the prior art, there remains a need for an effective treatment for GERD. It is an object of the present invention to provide a novel treatment and novel apparatus for the treatment of GERD.

II.

SUMMARY OF THE INVENTION

According to a preferred embodiment of the present invention, a method and apparatus are disclosed for treating gastro-esophageal reflux disease of a patient. The method includes accessing a juncture of an esophagus and a stomach of the patient on a distal side of a diaphragm. The esophagus and a fundus of the stomach intersect at a cardiac notch located at an original cardiac notch position. A reducing element is placed at the junction with the reducing element selected to re-shape the fundus to reposition the cardiac notch to a position more distal to a lower esophageal sphincter of the patient.

III.

IV.

DESCRIPTION OF THE PREFERRED EMBODIMENT

With reference now to the various drawing Figures in which identical elements are numbered identically throughout, a description of the preferred embodiment of the present invention will now be described.

Figure 1:
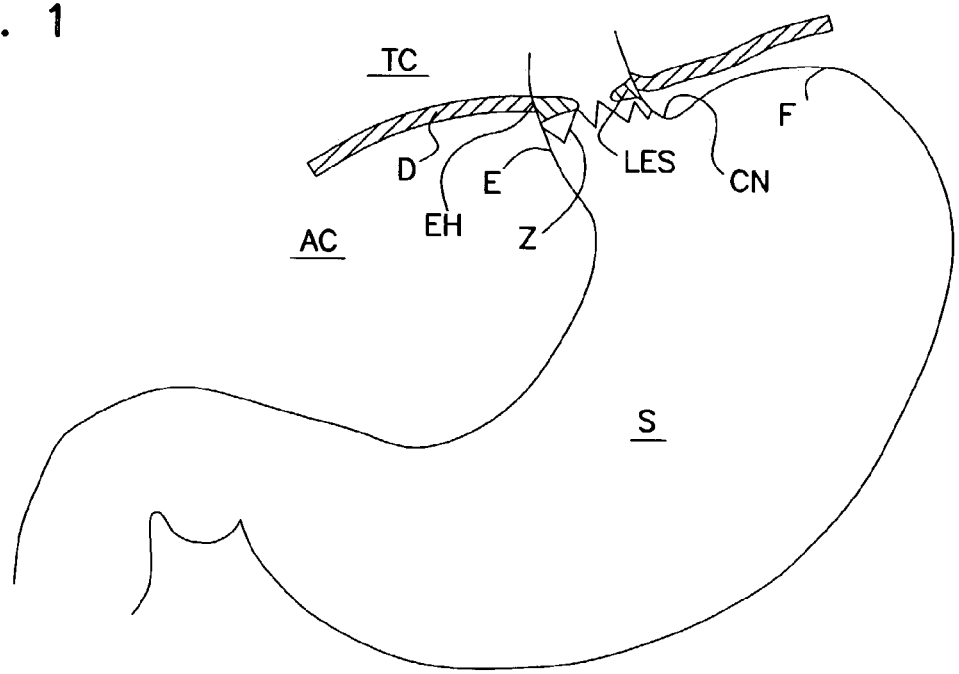
FIG. 1 is a schematic side view of a patient's stomach showing a diaphragm and location of a lower esophageal sphincter.

With initial reference to FIG. 1, relevant portions of a patient's gastrointestinal tract are schematically shown for ease of illustration. A lower esophageal sphincter LES is shown positioned within the esophagus E in the region of the diaphragm D. In FIG. 1, the LES is shown exaggerated for the purpose of illustration. The esophagus passes through an esophageal hiatus EH in the diaphragm D. The lower esophageal sphincter LES normally provides control of reflux of contents of the stomach S into the esophagus E.

The internal lining of the esophagus E has a cell structure substantially different from the internal lining of the stomach S. The internal lining of the stomach S is substantially thicker than that of the esophagus E. Further, the internal lining of the stomach S is comprised of cells which are much more tolerant to the presence of an acidic environment. These linings merge at the so-called Z-line near the LES.

In a patient having serious GERD disease, the LES is incompetent. Many prior art techniques attempt to treat the LES area. However, surgical treatment in this area is troublesome. Some patients suffer from a hiatus hernia where a lower portion of the esophagus E or an upper portion of the stomach S is protruded past the diaphragm D through the passage EH normally provided for the esophagus E. Treatment of this condition requires access to the thoracic cavity TC of the patient. It is preferred that GERD surgeries be limited to the abdominal cavity AC. Also, at the hiatus EH, the esophagus E is in very close proximity to major blood vessels and nerves (not shown) which are passing through the hiatus EH. Gray, *Anatomy of the Human Body*, 3$^{rd}$ Ed. (Clemente editor) (Lea & Febiger Publ., Philadelphia) page 1446 (1985). A surgical technique at the LES can result in injury to the blood vessels or nerves which would have serious consequences for the patient.

As shown in FIG. 1, the fundus F is an upper portion of the stomach S which joins with the esophagus E at an acute angle commonly referred to as the cardiac notch CN (also referred to as the angle of His). The present invention includes a reducing element 10 to effectively lengthen the esophagus E and lower the positioning of the cardiac notch CN. Also, formation of a reduced volume of a stomach above the re-positioned cardiac notch CN is avoided.

Figure 3:
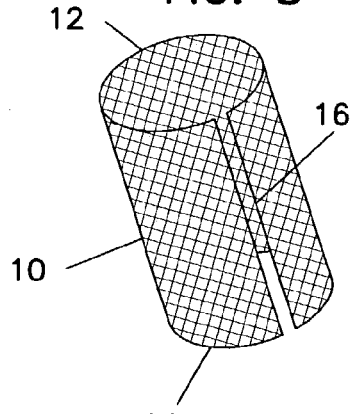
FIG. 3 is a perspective schematic view of the reducing element of FIG. 2.
Figure 2:
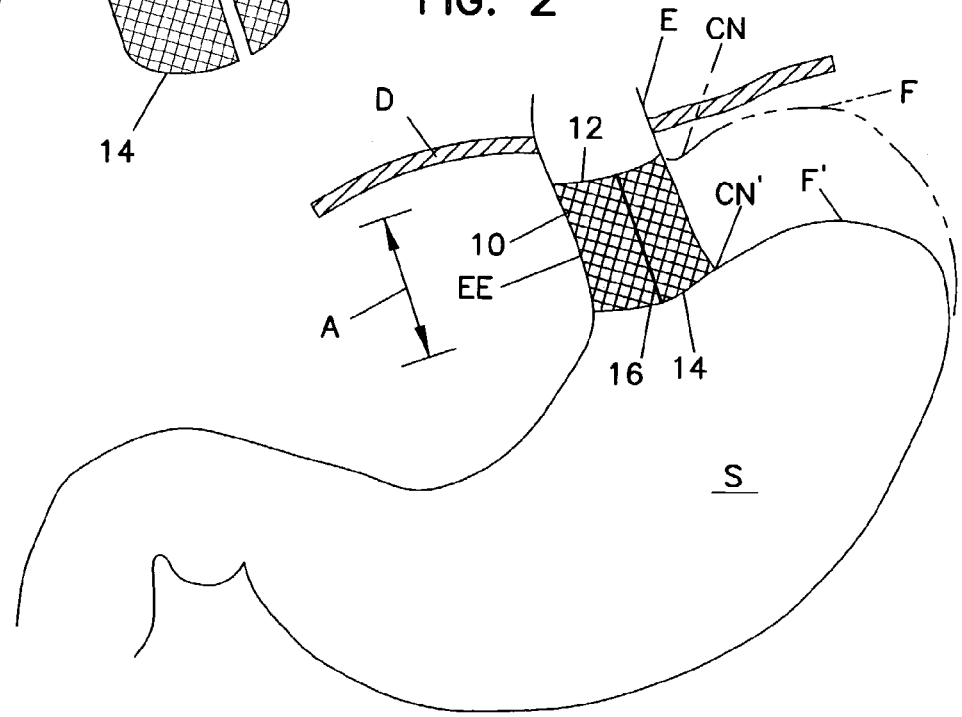
FIG. 2 is the view of FIG. 1 following placement of a first embodiment of a reducing element according to the present invention.

The reducing element 10 is schematically shown in FIGS. 2 and 3. In this embodiment, the reducing element 10 is a cylindrical wrap having an upper end 12 and a lower end 14. The upper end 12 is positioned surrounding the esophagus E in the region of the Z-line Z. The lower end 14 of the wrap 10 is positioned around the fundus F but is sized to be of substantially reduced volume compared to the rest of the volume of the fundus shown in FIG. 1. More specifically, the wrap 10 is a generally cylindrical shape sized to reduce the enclosed portion of the fundus F to re-shape the fundus and lower portion of the esophagus to define an extended esophageal portion EE.

In a preferred embodiment, the reducing element will be a mesh of biocompatible material having an open axially extending slot 16 which can be sutured along the cylindrical length of the reducing element 10 to permit a clinician to tighten up the portion of the fundus F surrounded by the reducing element 10. This will permit conforming the reducing element 10 to a size to create an effective extension of the esophagus EE for the reducing element 10 to maintain a substantially uniform interior cross-sectional diameter along its length from its upper end 12 to its lower end 14. This lowers the positioning of the cardiac notch CN to a repositioned location illustrated in FIG. 2. In FIG. 2, the new location of the cardiac notch CN' and the fundus F' are illustrated in the solid lines. The at-rest location (i.e., positioning of untreated features as shown in FIG. 1) of the cardiac notch CN and fundus F are indicated by phantom lines.

In use, the reducing element can be loosely placed about the esophagus and fundus, and then gathered and secured along a length of the element to compress the fundus and esophagus. Sutures or other tie members are used to set or control a diameter of the reducing element along the length of the element.

The upper and lower ends 12, 14 of the reducing element 10 may be sutured to opposing tissue to reduce the opportunity for migration of the reducing element. Since the reducing element 10 is being placed beneath the existing lower esophageal sphincter LES, dissection of the esophagus E near the diaphragm D is not required. This eliminates the need for surgical access to the thoracic cavity TC and avoids vessels and nerves closely proximate the esophagus E in the region of the hiatus EH.

In a preferred embodiment, the actual length (indicated by arrow A in FIG. 2) of the reducing element is approximately 3–4 centimeters to create an extended esophageal region EE of about 3–4 centimeters consistent with the length of the neo-esophagus of the Collis-Nissen gastroplasty procedure.

The material of the reducing element 10 can be any biocompatible material but preferably is a mesh of expanded polytetrafluoroethylene (ePTFE). The mesh may in part or in whole be formed of polyester to increase integration of the reducing element 10 into opposing tissue. Selected areas of polyester create selected areas of tissue in-growth (and others of non-in-growth) to permit severing selected ones of non-in-growth and in-growth areas to effectively reverse the procedure should complications arise. Alternatively, a polyester mesh could be provided with portions impregnated with silicone rubber.

By creating an extended length EF of the esophagus E, resistance to reflux has been created. Further, the extended length EE of the esophagus is formed of material of a thickened tissue wall (relative to the tissue of the esophagus E above the Z-line Z), and of a composition which is more tolerant of an acidic environment.

While the above features alone may provide adequate efficacy for many patients, in some patients the degree of incompetency of the lower esophageal sphincter LES may be so great that additional resistance to reflux may be required. In such patients a restriction element 20 can be incorporated into the reducing element 10.

Figure 4:
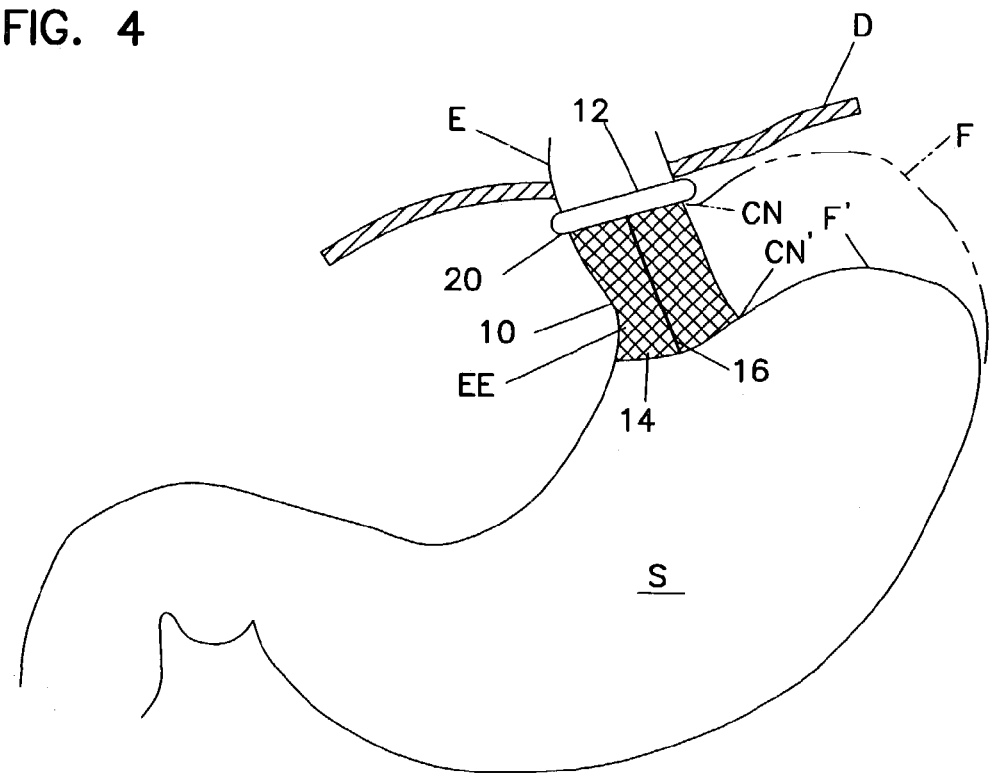
FIG. 4 is the view of FIG. 2 showing the reducing element provided with an optional restriction member.

FIG. 4 illustrates the use of the reducing element of FIG. 2 in combination with a restricting element 20. The restricting element 20 may be a passive constricting ring such as those shown in U.S. Pat. Nos. 5,006,106 and 5,919,233 (both incorporated herein by reference). Alternatively, the restricting element may be an adjustable artificial sphincter such as that shown in U.S. Pat. No. 6,432,040 (incorporated herein by reference) or a mechanically operated sphincter such as those shown in U.S. Pat. No. 6,074,341 (incorporated herein by reference).

Figure 5:
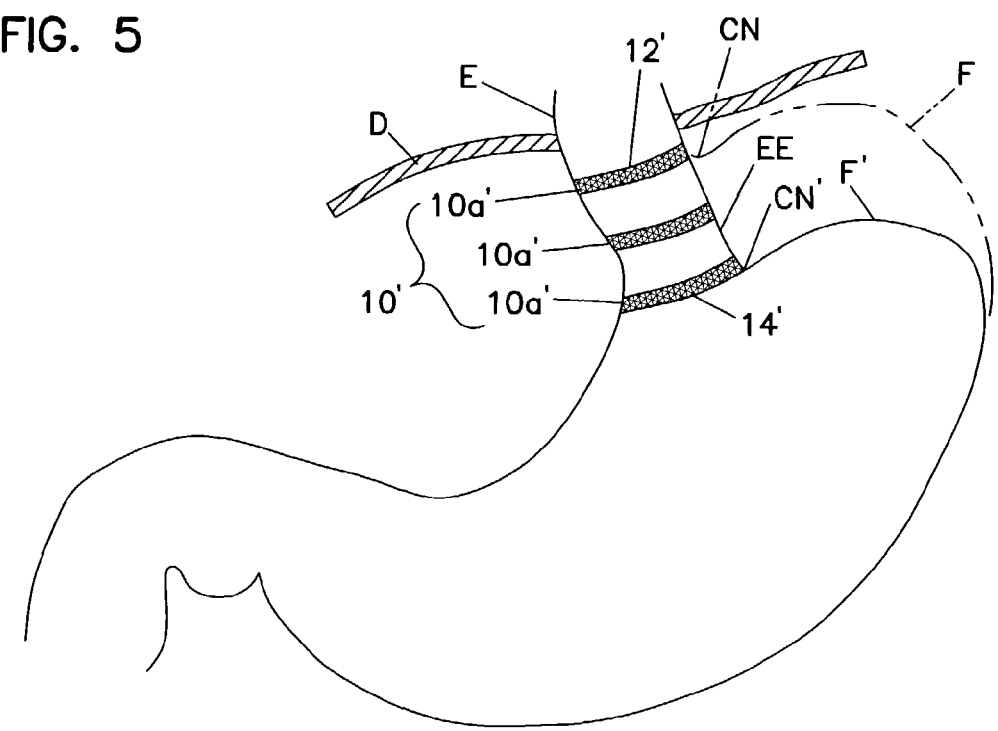
FIG. 5 is a view of a second embodiment of a reducing element according to the present invention.

FIG. 5 shows a second embodiment of a reducing element 10' where the embodiment of FIG. 5 is formed of multiple bands 10a' placed around the extended esophageal length. It will be noted that in each of the embodiments of FIGS. 2 and 5, the portion of the extended esophagus EE between the upper and lower ends 12, 14 and 12', 14' is restrained from forming an enlarged area or chamber to act as a collection of food and create a sensation of satiation for the patient.

Figure 6:
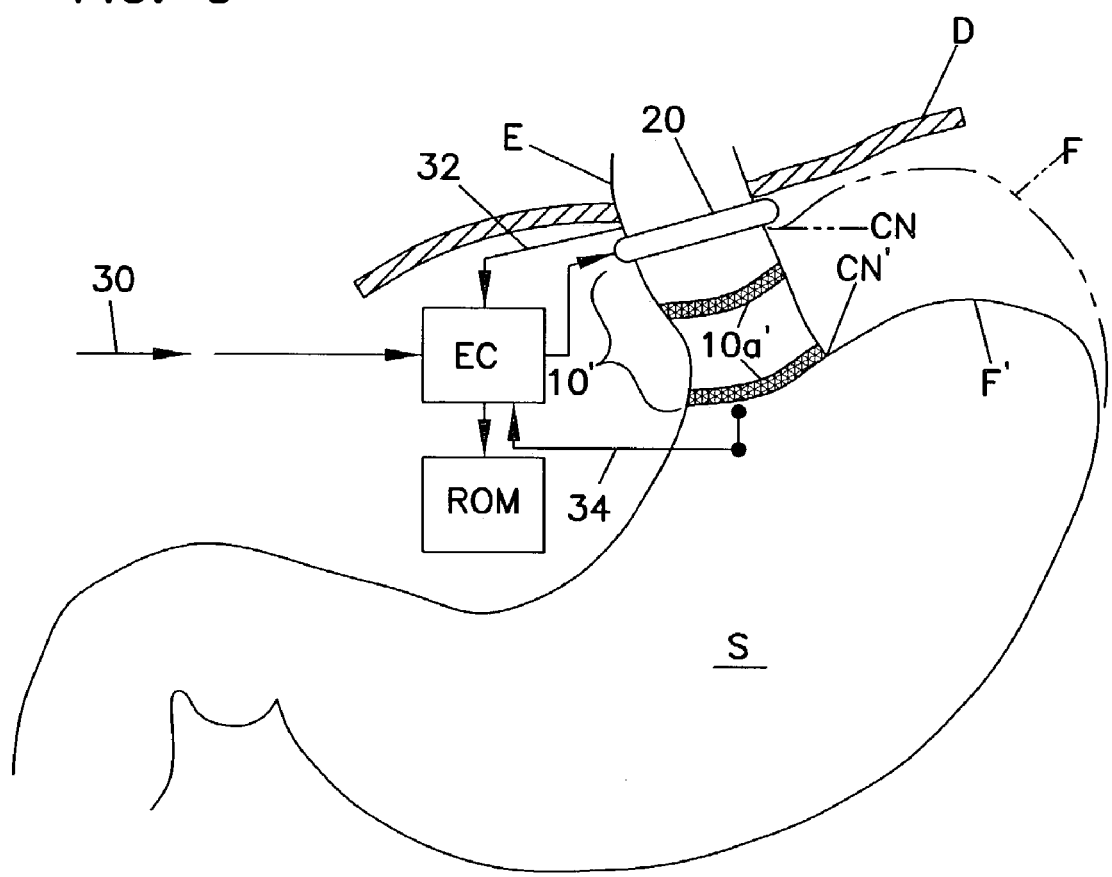
FIG. 6 is the view of FIG. 5 showing the reducing element provided with an optional restriction member and where the restriction member is an adjustable member and showing various feedback mechanisms and control mechanisms for controlling the restriction member.

In artificial adjustable sphincters, the amount of restriction of the sphincter can be adjusted by either the patient directly (as shown in U.S. Pat. No. 6,432,040) or can be adjusted by internal actuators such as stepper motors of the like driving mechanically adjustable sphincters such as those shown in U.S. Pat. No. 6,074,341. Control mechanisms for such sphincters are schematically shown in FIG. 6 in use with an artificial sphincter 20 in combination with the element 10'. It will be appreciated such controls could also be used with an artificial sphincter 20 in the embodiment of FIG. 4.

In each of FIGS. 4 and 6, the restricting element 20 is adjacent the upper end 12 of the reducing element 10, 10'. It will be appreciated the element 20 may be positioned near the lower end 14 or at any intermediate location.

The patient can control constriction and relaxation of the artificial sphincter 20 directly as indicated by a patient input 30 to an electronic controller EC which may be implanted in the patient. In FIG. 6, the patient input 30 is shown as an arrow not directly connected to the controller EC to illustrate the input 30 may be a radio frequency or inductive coupling through the skin to the implanted controller EC.

The electronic controller EC may include access to read-only memory ROM for inputting maximum expansion and minimum constriction sizes for the artificial sphincter 20 with the device having a default restriction for a maximum opening of the esophagus. Also, baro-sensors or other sensors may be placed on the esophagus E above or below (or both) the artificial sphincter 20. Such sensors provide an input 32, 34 to the electronic controller. The signal above the artificial sphincter 20 indicates the presence of food or drink in the esophagus E requiring opening of the artificial sphincter 20. The signal below the artificial sphincter 20 (for example, a strain signal) indicates the presence of gas or stomach contents requiring opening of the artificial sphincter 20, (for example for belching).

With the present invention, dissection of the esophagus E in the region of the diaphragm D and in the region in close proximity to nerves and blood vessels passing near the hiatus EH have been avoided. The lengthening of the esophagus with the reducing element 10 extends the length of the esophagus to create an enhanced resistance to reflux of stomach content. Further, the extended esophageal region EE is comprised of cell linings which are more tolerant of acidic content and of greater wall thickness. The greater wall thickness is of additional advantage in combination with a device 20. The greater wall thickness can better tolerate a mechanical opposition of the device 20.

With the foregoing detailed description of the present invention, it has been shown how the objects of the invention have been attained in a preferred manner. Modifications and equivalents of disclosed concepts such as those which might readily occur to one skilled in the art, are intended to be included in the scope of the claims which are appended hereto.

What is claimed is:

1. A method for treating gastro-esophageal reflux disease (GERD) of a patient comprising:
   accessing a juncture of an esophagus and a stomach of the patient on a distal side of a diaphragm of the patient with said esophagus and a fundus of said stomach intersecting at a cardiac notch located at an original cardiac notch position;
   treating the patient's GERD by placing a reducing element at said junction with said reducing element selected to reposition said cardiac notch to a repositioned cardiac notch position more distal to a lower esophageal sphincter of said patient and define an extended esophageal portion;
   said reducing element sized for said reducing element to be placed around both a distal portion of said esophagus and a proximal portion of said stomach with said reducing element sized to surround a portion of said esophagus above said original cardiac notch portion and said proximal portion of said stomach, said placing including placing said reducing element around both said esophagus and said stomach with said reducing element surrounding a portion of said esophagus above said original cardiac notch portion and said proximal portion of said stomach to create said extended esophageal portion and with said reducing element restraining formation of a gastric pouch between proximal and distal ends of said reducing element.

2. A method according to claim 1 wherein said reducing element comprises a plurality of separate elements disposed serially along said extended esophageal portion.

3. A method according to claim 1 wherein said placing includes selecting said element to be selectively adjustable along a length of said element to selectively adjust a volume of said element to form an extended esophagus portion between said original cardiac notch position and said repositioned cardiac notch position.

4. A method for treating gastro-esophageal reflux disease (GERD) of a patient comprising:
   accessing a juncture of an esophagus and a stomach of the patient on a distal side of a diaphragm of the patient with said esophagus and a fundus of said stomach intersecting at a cardiac notch located at an original cardiac notch position;
   placing a reducing element at said junction with said reducing element selected to reposition said cardiac notch to a repositioned cardiac notch position more distal to a lower esophageal sphincter of said patient and define an extended esophageal portion;
   wherein said placing includes selecting said element to be selectively adjustable along a length of said element to selectively adjust a volume of said element to form an extended esophagus portion between said original cardiac notch position and said repositioned cardiac notch position; and
   wherein said element includes a slit along a length thereof and said adjusting includes altering a spacing of said slit.

5. A method according to claim 3 wherein said element includes a material positioned loosely on said esophagus and fundus and said adjusting includes gathering and securing said gathered material along a length of said element.

6. A method according to claim 1 wherein said element is secured to either said esophagus or said stomach to restrict movement of said element relative to a final positioning of said element.

7. A method according to claim 6 wherein said securing includes providing selected areas of said element with tissue in-growth areas.

8. A method according to claim 1 further comprising placing an implant adjacent an esophagus of said patient to create a restricted region.

9. A method according to claim 8 wherein said implant can be actuated to at least partially close said esophagus and abate reflux of contents of a stomach of said patient retrograde within said esophagus.

10. A method according to claim 9 wherein said actuation of said implant includes actuating an artificial sphincter at least partially surrounding said esophagus to change states from an open state to an at least partially closed state, said artificial sphincter in said open state permitting substantially unimpeded food flow through said esophagus into said stomach, said artificial sphincter in said at least partially closed position at least partially closing said esophagus and abating reflux of contents of said stomach retrograde within said esophagus.

11. A method according to claim 8 wherein said actuation of said implant is initiated by said patient.

12. A method according to claim 8 wherein said actuation of said implant is initiated by a controller operatively connected to electrodes and having an input operatively connected to organ sensors.

* * * * *